United States Patent [19]

Dierdorf et al.

[11] Patent Number: 5,631,403
[45] Date of Patent: May 20, 1997

[54] PROCESS FOR THE PREPARATION OF HYDROXYCARBOXANILIDES

[75] Inventors: Andreas Dierdorf, Frankfurt; Siegfried Planker, Königstein; Theodor Papenfuhs, Frankfurt, all of Germany

[73] Assignee: Hoechst AG, Frankfurt, Germany

[21] Appl. No.: 493,272

[22] Filed: Jun. 21, 1995

[30] Foreign Application Priority Data

Jun. 23, 1994 [DE] Germany .................. 44 21 884.2

[51] Int. Cl.⁶ .................. C07C 233/05; C07C 233/88
[52] U.S. Cl. .................. 564/202; 564/201
[58] Field of Search .................. 564/202, 201

[56] References Cited

U.S. PATENT DOCUMENTS

| 4,219,681 | 8/1980 | Schwenk et al. | 568/842 |
| 4,334,073 | 6/1982 | Diehr | 546/245 |
| 4,440,780 | 4/1984 | Chan | 424/275 |
| 4,500,740 | 2/1985 | House | 568/796 |

FOREIGN PATENT DOCUMENTS

| 0008096 | 2/1980 | European Pat. Off. . |
| 0064486 | 11/1982 | European Pat. Off. . |
| 2904490 | 8/1980 | Germany . |
| 3038598 | 5/1982 | Germany . |
| 3539394 | 5/1987 | Germany . |

OTHER PUBLICATIONS

European Search Report No. 95109415, Aug. 11, 1995.

*Primary Examiner*—Shailendra Kumar
*Attorney, Agent, or Firm*—Connolly & Hutz

[57] ABSTRACT

The present invention relates to a process for the preparation of hydroxycarboxanilides of the formula (1)

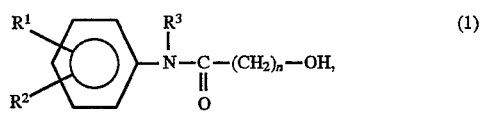

in which $R^1$ and $R^2$ are identical or different and are hydrogen, halogen, a nitro group, a cyano group, a straight-chain or branched alkyl, alkenyl, alkynyl or alkoxy group having 1 to 12 carbon atoms, an aralkyl group having 7 to 12 carbon atoms, a cycloalkyl group having 6 to 12 carbon atoms or an aryl group having 6 to 12 carbon atoms, $R^3$ is hydrogen or a straight-chain or branched alkyl group having 1 to 12 carbon atoms and n is an integer from 1 to 12, by reacting a halocarboxanilide of the formula (2)

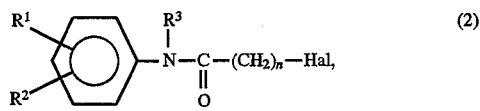

in which $R^1$, $R^2$, $R^3$ and n have the same meaning as in formula (1) and Hal is chlorine, bromine or iodine, with a basic compound in a solvent mixture comprising water and one or more polar aprotic solvents at a temperature of 40° to 180° C.

21 Claims, No Drawings

PROCESS FOR THE PREPARATION OF HYDROXYCARBOXANILIDES

The present invention relates to a novel process for the preparation of hydroxycarboxanilides which starts from the corresponding halocarboxanilides and is an improvement of the prior art.

Hydroxycarboxanilides, in particular glycolanilides, are an important group of compounds and function as important precursors for the preparation of herbicides (EP-A-300 344) and pharmaceutically active compounds (EP-A-284 338, EP-A-363 284) as well as for the preparation of fungicides (U.S. Pat. No. 4,440,780).

Since this group of compounds is so important, there has been no lack of attempts in the past to make hydroxycarboxamides and, in particular hydroxycarboxanilides, accessible by a variety of routes.

For instance, DE-A-3 038 598 discloses a process for the preparation of α-hydroxycarboxamides by reacting α-oxycarboxamides, in particular the corresponding formyloxy compounds, with alcohols in the presence of catalytic amounts of hydroxides, hydrogen carbonates or carbonates of alkali metals or alkaline earth metals. As a result of the transesterification which takes place, the corresponding α-hydroxycarboxamides are formed. Since the α-oxycarboxamides required for the reaction have to be prepared in a separate step by reacting α-chlorocarboxamides with alkali metal formates, the preparation of the α-hydroxycarboxamides—starting from the corresponding α-chlorocarboxamides—is in reality a two-step process which has the added disadvantage that the α-oxycarboxamides are prepared in the presence of a quaternary ammonium salt because it is known that such quaternary ammonium salts result in problems with the treatment of waste water.

A further process for the preparation of α-hydroxycarboxamides can be found in DE-A-2 904 490. In this case, α-halocarboxamides are reacted, in a first step, with an alkali metal acetate or alkaline earth metal acetate in the presence of a quaternary ammonium salt and, if appropriate, using a diluent to give the corresponding α-acetoxycarboxamides, and the α-acetoxycarboxamides are deacylated by reacting them with an alcohol in the presence of catalytic amounts of an alkali metal hydroxide, alkaline earth metal hydroxide, alkali metal carbonate or alkaline earth metal carbonate. Again, this process represents a two-step procedure in which the use of quaternary ammonium salts, again, results in undesirable pollution of the waste water.

DE-A-3 539 394 likewise relates to a two-step process for the preparation of glycolamides, by reacting chloroacetamides with potassium carbonate in the presence of an aprotic amide as the diluent and if appropriate in the presence of a phase transfer catalyst to give symmetric carbonates which are deacylated either after previous isolation in a separate, second step or without intermediate isolation directly by reaction with a primary alcohol by transesterification in the presence of an alkali metal hydroxide. However, all examples describe a process being carried out in the presence of a phase transfer catalyst. Moreover, the yields, which are fairly low in some cases (22 to 80%), still leave something to be desired.

The above described processes are relatively complicated since they make accessible the desired hydroxycarboxamides via two separate reaction steps which proceed in succession. Moreover, the quaternary ammonium salts which are used as phase transfer catalysts cause problems with the waste products formed during the reaction. They are undesirable in the waste water particularly because of their unfavorable properties.

Bearing in mind the importance of hydroxycarboxanilides, it is a rewarding task to provide a process for the preparation of hydroxycarboxanilides which avoids the disadvantages of the abovementioned processes, can be carried out in a simple manner using readily accessible starting materials and auxiliaries and, moreover, results in less waste.

This task is achieved by a process for the preparation of hydroxycarboxanilides of the formula (1)

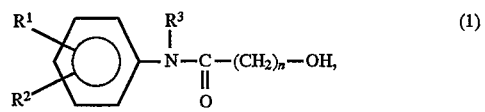

in which $R^1$ and $R^2$ are identical or different and are hydrogen, halogen, a nitro group, a cyano group, a straight-chain or branched alkyl, alkenyl, alkynyl or alkoxy group having 1 to 12 carbon atoms, an aralkyl group having 7 to 12 carbon atoms, a cycloalkyl group having 6 to 12 carbon atoms or an aryl group having 6 to 12 carbon atoms, $R^3$ is hydrogen or a straight-chain or branched alkyl group having 1 to 12 carbon atoms and n is an integer from 1 to 12. It comprises reacting a halocarboxanilide of the formula (2)

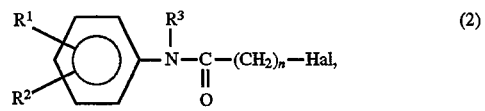

in which $R^1$, $R^2$, $R^3$ and n have the same meaning as in formula (1) and Hal is chlorine, bromine or iodine, with a basic compound in a solvent mixture comprising water and one or more polar aprotic solvents at a temperature of 40° to 180° C.

The process according to the invention has a number of advantages. First, it yields the desired hydroxycarboxanilide in a single reaction step and, secondly, the use of phase transfer catalysts can generally be dispensed with. Moreover, the process according to the invention requires relatively short reaction times and makes accessible the desired products of value in high yields and also high purity. It can be realized without being too complex technically and using readily accessible starting materials.

A further advantage is the fact that the solvent mixture which is composed of water and one or more polar aprotic solvents can be removed by distillation once the reaction has ended and reused for the reaction. The number and amount of waste product is reduced, since only a halide is formed in this reaction as the single waste product.

It is highly surprising that the reaction does not result in the formation of undesirable by-products, or only to a limited extent. In particular, it might have been expected that ethers would be formed by the reaction of previously formed hydroxycarboxanilides with as yet unreacted halocarboxanilides in the presence of basic compounds. Surprisingly, the formation of such ethers can be prevented almost completely, or to a substantial extent, by controlling the reaction appropriately.

The reaction proceeds as shown in the following equation:

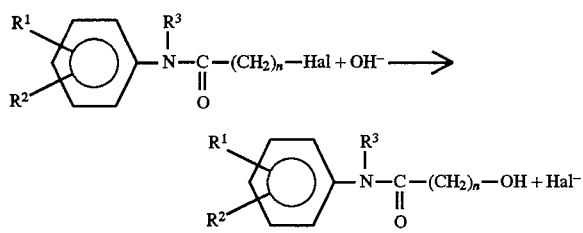

The halocarboxanilides required for the reaction can be prepared in a relatively uncomplicated manner by reacting an ω-halocarboxylic acid chloride or an ω-halocarboxylic acid bromide with an aniline containing the radicals $R^1$, $R^2$ and $R^3$. Particularly readily accessible compounds are the chloroacetyl anilides, which are obtained by reacting chloroacetyl chloride with the corresponding aniline derivative.

Without laying claim to completeness, examples of suitable anilines which may be mentioned are 2-methoxyaniline, 4-methoxyaniline, 3,5-dimethylaniline, 2-chloroaniline, 4-chloroaniline, N-methylaniline, N-ethylaniline, N-isopropylaniline and N-isopropyl-4-fluoroaniline and examples of suitable ω-halocarboxylic acid halides which may be mentioned are chloroacetyl chloride, chloroacetyl bromide, ω-chloropropionyl chloride, ω-chloropropionyl bromide and ω-bromovaleryl chloride.

In the process according to the invention, a halocarboxanilide of the formula (2) is used in which $R^1$, $R^2$, $R^3$, n and Hal are as defined above.

A compound which can be employed very successfully is a halocarboxanilide of the formula (2) in which $R^1$ and $R^2$ are identical or different and are hydrogen, halogen, a nitro group, a straight-chain or branched alkyl or alkoxy group having 1 to 4 carbon atoms or an aralkyl group having 7 to 12 carbon atoms, in particular hydrogen, fluorine, chlorine, bromine or an alkyl or alkoxy group having 1 to 4 carbon atoms, preferably hydrogen, fluorine, chlorine, bromine or an alkyl group having 1 to 4 carbon atoms.

Another substance which can be employed very successfully is a halocarboxanilide of the formula (2) in which $R^3$—independently of the respective meaning of $R^1$ and $R^2$—is hydrogen or a straight-chain or branched alkyl group having 1 to 4 carbon atoms, in particular an isopropyl group.

As has been mentioned at the outset, n is an integer from 1 to 12, but in particular an integer from 1 to 4, preferably 1. As already mentioned above, Hal is chlorine, bromine or iodine, but in particular chlorine or bromine, preferably chlorine.

Substances which may be mentioned as a selection of some suitable ω-halocarboxanilides are, for example, 2-methoxychloroacetanilide, 4-methoxychloroacetanilide, 3,5-dimethylchloroacetanilide, 4'-fluoro-N-isopropylchloroacetanilide, N-methylchloroacetanilide, 2'-chloro-ω-bromovaleranilide and 4'-chloro-ω-bromovaleranilide.

Suitable basic compounds are generally all substances which release hydroxide ions from the solvent mixture formed by water and the polar aprotic solvent. These include metal hydroxides, in particular alkali metal hydroxides and alkaline earth metal hydroxides, basic salts, in particular alkali metal hydrogen carbonates, alkaline earth metal hydrogen carbonates, alkali metal carbonates, alkaline earth metal carbonates, alkali metal carboxylates, alkaline earth metal carboxylates, in particular alkali metal salts and alkaline earth metal salts of carboxylic acids having 1 to 6 carbon atoms, in particular of aliphatic mono- or dicarboxylic acids having 1 to 4 carbon atoms, and mixtures of the abovementioned substances.

Particularly suitable substances are sodium carbonate, potassium carbonate and sodium acetate, in particular sodium carbonate or potassium carbonate.

To prepare the solvent mixture, the ratio by weight of water to polar aprotic solvent can be within a relatively wide range. In most cases, it suffices to use water and polar aprotic solvent in a ratio by weight of 1:4 to 4:1, in particular 1:2 to 2:1.

Without laying claim to completeness, substances which can be used as polar aprotic solvent are for example N,N-dimethylformamide, N,N-dimethylacetamide, formamide, tetrahydrofuran, dioxane, dimethyl sulfoxide, N-methylpiperidone or N-methylpyrrolidone or mixtures of these, in particular N,N-dimethylacetamide or N-methylpyrrolidone.

Even though the reaction can also be carried out with a substoichiometric amount of basic compound relative to the halocarboxanilide, the basic compound and the halocarboxanilide will be used in a stoichiometric ratio or in an excess, for economic reasons. In general, 1 to 5 equivalents of the basic compound are employed per mole of halocarboxanilide. Frequently, it suffices to employ 1 to 1.25 equivalents of the basic compound per mole of halocarboxanilide.

As mentioned at the outset, the reaction is generally carried out at 40° to 180° C. In most cases, it has proved sufficient to react the halocarboxanilide at 60 to 140, in particular 70° to 120° C. The process is carried out under atmospheric pressure or the reaction pressure which is established in each case under the reaction conditions.

After the reaction has ended, the solvent mixture, which is composed of water and the polar aprotic solvent, or solvents, is usually removed by distillation, if appropriate under reduced pressure, and the residue obtained is distilled under a high vacuum.

However, the distillation step under a high vacuum can also be dispensed with and the residue obtained after the solvent mixture has been removed can be extracted using a suitable organic solvent, if appropriate together with water, and the organic phase which contains the desired product of value can be washed with water, the aqueous phase separated off and the organic phase subsequently dried.

Suitable organic solvents are, inter alia, chlorinated aliphatic or aromatic hydrocarbons, for example methylene chloride, dichloroethane, chloroform, chlorobenzene, dichlorobenzene, chlorotoluene or aromatic hydrocarbons, for example toluene, o-xylene, m-xylene, p-xylene, mixtures of xylene isomers, ethylene benzene, mesitylene. Mixtures of other varieties of the abovementioned solvents may also be used. Particularly suitable are methylene chloride, toluene, chloroform, o-xylene, m-xylene, p-xylene or mixtures of xylene isomers.

The further purification of the residue in the organic solvent is carried out by crystallization, if appropriate after concentrating the organic phase.

The invention furthermore relates to the compound N-hydroxyacetyl-3,5-dimethylaniline, which is a valuable precursor for the preparation of herbicides, pharmaceutically active compounds and fungicides.

The examples which follow describe the invention without imposing a restriction.

Experimental part

COMPARISON EXAMPLES 1 AND 2 AND EXAMPLES 1 AND 2

Preparation of N-hydroxyacetyl-N-isopropyl-(4-fluoroaniline)

In a 500 ml flask, 23.0 g (0.1 mol) of N-chloroacetyl-N-isopropyl-4-fluoroaniline and 11.7 g (0.11 mol) of sodium carbonate in 340 ml of solvent or solvent mixture are heated with stirring to reflux temperature (100° C.). The reaction is monitored by gas chromatography (sampling after in each case 1 hour). The results are compiled in the table which follows.

TABLE 1

| | Solvent | Solvent mixture | Yield* (after a reaction time of 1 hour) |
|---|---|---|---|
| Comparison Example 1 | 340 ml of water | — | 29.4% |
| Comparison Example 2 | 340 ml of N-methyl-pyrrolidone | — | 1.7% |
| Example 1 | — | 200 ml of N-methyl-pyrrolidone + 140 ml of water | 84.7% |
| Example 2 | — | 200 ml of N,N-dimethylacetamide + 140 ml of water | 73.2% |

*N-hydroxyacetyl-N-isopropyl-(4-fluoroaniline) determined by GC analysis of the reaction mixture As shown by the above results, the process according to the invention (Examples 1 and 2) give significantly better results than a procedure which involves the use of water but no polar aprotic solvent (Comparison Example 1) or a procedure which involves the use of a polar aprotic solvent (N-methylpyrrolidone), but no water (Comparison Example 2).

EXAMPLE 3

Preparation of N-hydroxyacetyl-N-isopropyl-(4-fluoroaniline)

In a suitable apparatus (500 ml flask), 23.0 g (0.1 mol) of N-chloroacetyl-N-isopropyl-4-fluoroaniline and 11.7 g (0.11 mol) of sodium carbonate are refluxed (100° C.) in a solution of 140 ml of water and 200 ml of N-methylpyrrolidone. After 2.5 hours, the solvent mixture is stripped off in vacuo and the residue distilled at 2 to 3 torr and 132° to 135° C. This gives 18.1 g (86% of theory) of N-hydroxyacetyl-N-isopropyl-(4-fluoroaniline) with a purity of 99.1% (GC).

EXAMPLE 4

Preparation of N-hydroxyacetyl-(3,5-dimethylaniline)

In a 1 l flask, 39.5 g (0.2 mol) of 3,5-dimethylchloroacetanilide (prepared from chloroacetyl chloride and 3,5-dimethylaniline) and 23.3 g (0.22 mol) of sodium carbonate are heated for 7 hours at 100° C. in a solvent mixture of 450 ml of N-methylpyrrolidone and 300 ml of water. After the N-methylpyrrolidone/water mixture has been distilled off, the residue is suspended in toluene and the toluene phase repeatedly washed with water to remove any remaining N-methylpyrrolidone. The toluene phase is subsequently filtered. Concentration in vacuo gives 30.5 g (85.1%) of N-hydroxyacetyl-3,5-dimethylaniline as colorless crystals with a melting point of 114° C. and a purity (GC) of 99.3%.

EXAMPLE 5

Preparation of 2-methoxy-hydroxyacetanilide

In a 250 ml flask, 10 g (0.05 mol) of 2-methoxy-chloroacetanilide (prepared from chloroacetyl chloride and 2-methoxyaniline) and 6 g (0.55 mol) of sodium carbonate are heated at 100° C. in a solvent mixture of 100 ml of N-methylpyrrolidone and 70 ml of water. A GC check after a reaction time of 6 hours reveals a yield of 70% of 2-methoxy-hydroxyacetanilide and 5.5% of 2-methoxydiglycolanilide.

What is claimed is:

1. A process for the preparation of hydroxycarboxanilides of the formula (1)

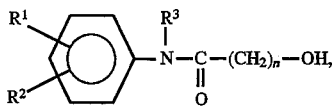

(1)

in which $R^1$ and $R^2$ are identical or different and are hydrogen, halogen, a nitro group, a cyano group, a straight-chain or branched alkyl, alkenyl, alkynyl or alkoxy group having 1 to 12 carbon atoms, an aralkyl group having 7 to 12 carbon atoms, a cycloalkyl group having 6 to 12 carbon atoms or an aryl group having 6 to 12 carbon atoms, $R^3$ is hydrogen or a straight-chain or branched alkyl group having 1 to 12 carbon atoms and n is an integer from 1 to 12, which comprises reacting a halocarboxanilide of the formula (2)

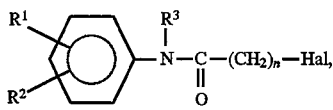

(2)

in which $R^1$, $R^2$, $R^3$ and n have the same meaning as in formula (1) and Hal is chlorine, bromine or iodine, with a basic compound in a solvent mixture comprising water and one or more polar aprotic solvents at a temperature of 40° to 180° C.

2. The process as claimed in claim 1, wherein a halocarboxanilide of the formula (2) is employed in which $R^1$ and $R^2$ are identical or different and are hydrogen, halogen, a nitro group, a straight-chain or branched alkyl or alkoxy group having 1 to 4 carbon atoms or an aralkyl group having 7 to 12 carbon atoms.

3. The process as claimed in claim 1, wherein a halocarboxanilide of the formula (2) is employed in which $R^1$ and $R^2$ are identical or different and are hydrogen, fluorine, chlorine, bromine or an alkyl or alkoxy group having 1 to 4 carbon atoms.

4. The process as claimed in claim 1, wherein a halocarboxanilide of the formula (2) is employed in which $R^1$ and $R^2$ are identical or different and are hydrogen, fluorine, chlorine, bromine or an alkyl group having 1 to 4 carbon atoms.

5. The process as claimed in claim 1, wherein a halocarboxanilide of the formula (2) is employed in which $R^3$ is hydrogen or a straight-chain or branched alkyl group having 1 to 4 carbon atoms.

6. The process as claimed in claim 1, wherein a halocarboxanilide of the formula (2) is employed in which $R^3$ is an isopropyl group.

7. The process as claimed in claim 1, wherein a halocarboxanilide of the formula (2) is employed in which n is an integer from 1 to 4.

8. The process as claimed in claim 1, wherein a halocarboxanilide of the formula (2) is employed in which n is 1.

9. The process as claimed in claim 1, wherein a halocarboxanilide of the formula (2) is employed in which Hal is Cl or Br.

10. The process as claimed in claim 1, wherein a halocarboxanilide of the formula (2) is employed in which Hal is chlorine.

11. The process as claimed in claim 1, wherein the basic compound employed is a hydroxide, hydrogen carbonate, carbonate and/or carboxylate of an alkali metal or alkaline earth metal.

12. The process as claimed in claim 1, wherein the basic compound employed is sodium carbonate, potassium carbonate or sodium acetate.

13. The process as claimed in claim 1, wherein the solvent mixture employed is water and polar aprotic solvent in a ratio by weight of 1:4 to 4:1.

14. The process as claimed in claim 1, wherein the solvent mixture employed is water and polar aprotic solvent in a ratio by weight of 1:2 to 2:1.

15. The process as claimed in claim 1, wherein the polar aprotic solvent employed is N,N-dimethylformamide, N,N-dimethylacetamide, formamide, tetrahydrofuran, dioxane, dimethyl sulfoxide, N-methylpiperidone or N-methylpyrrolidone, or mixtures of these.

16. The process as claimed in claim 1, wherein the polar aprotic solvent employed is N,N-dimethylacetamide or N-methylpyrrolidone.

17. The process as claimed in claim 1, wherein 1 to 5 equivalents of the basic compound are employed per mole of halocarboxanilide.

18. The process as claimed in claim 1, wherein 1 to 1.25 equivalents of the basic compound are employed per mole of halocarboxanilide.

19. The process as claimed in claim 1, wherein the halocarboxanilide is reacted at a temperature from 60° to 140° C.

20. The process as claimed in claim 1, wherein the halocarboxanilide is reacted at a temperature from 70° to 120° C.

21. The process as claimed in claim 1, wherein the reaction is a one step reaction.

* * * * *